United States Patent [19]

Kennedy

[11] Patent Number: 5,312,249

[45] Date of Patent: May 17, 1994

[54] UNBREAKABLE DISPOSABLE PHOTOCURING GUIDE

[76] Inventor: John Kennedy, 23 Mollison Court, Guelph, Ontario, Canada, N1C 1A7

[21] Appl. No.: 956,380

[22] Filed: Oct. 5, 1992

[51] Int. Cl.⁵ .............................. A61C 1/00; A61C 3/00
[52] U.S. Cl. ........................................ 433/29; 433/229
[58] Field of Search ................... 433/29, 299; 206/63.5

[56] References Cited

U.S. PATENT DOCUMENTS

| | | | |
|---|---|---|---|
| 4,020,556 | 5/1977 | Sotman | 433/29 |
| 4,588,089 | 5/1986 | Yanz, Jr. et al. | 206/581 |
| 4,836,782 | 6/1989 | Gonser | 433/229 |
| 4,867,305 | 9/1989 | Schneider | 206/63.5 |
| 5,002,361 | 3/1991 | De Martino et al. | 350/96.34 |
| 5,098,292 | 3/1992 | Lazarof | 433/141 |

FOREIGN PATENT DOCUMENTS

| | | | |
|---|---|---|---|
| 0240007 | 10/1987 | European Pat. Off. | 433/29 |
| 0371381 | 6/1990 | European Pat. Off. | 433/29 |
| 253997 | 4/1970 | U.S.S.R. | 433/29 |

Primary Examiner—Gene Mancene
Assistant Examiner—Cindy A. Cherichetti
Attorney, Agent, or Firm—David W. Wong

[57] ABSTRACT

A disposable dental curing light guide which can be made of a low cost polymer. The light guide can be radioactively sterilized and packed in a sterilized dispensing envelope to maintain it in a sterilized and clean state. The light guide can provide satisfactory transmission of light between 400 nm and 500 nm for dental curing purposes.

1 Claim, 1 Drawing Sheet

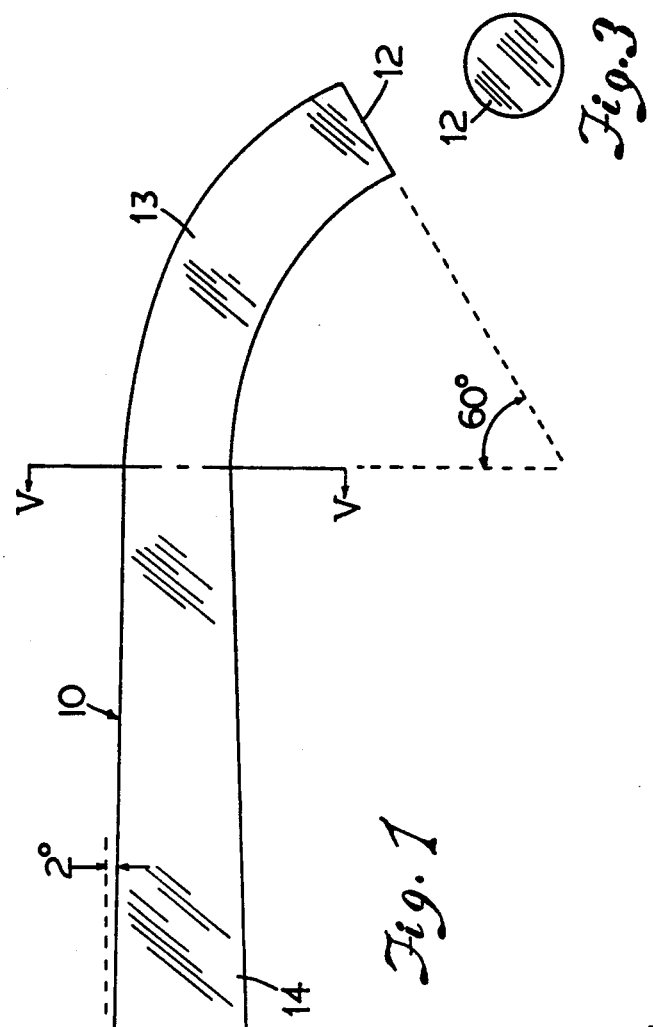
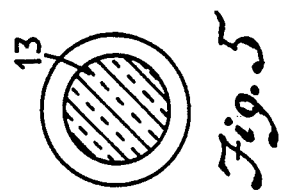
Fig.3
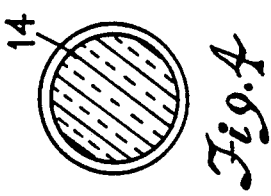
Fig.5
Fig.1
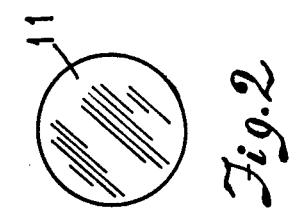
Fig.2

UNBREAKABLE DISPOSABLE PHOTOCURING GUIDE

BACKGROUND OF THE INVENTION

This invention relates to a light curing device and in particular to a disposable light guide or probe suitable for dental curing purposes.

In photocuring, particularly for dental photocuring purposes, commonly a stationary or Dartable light generating device is used. For convenience in manipulation, in the portable light generating device, light is provided by a hand-held gun unit which generates the light suitable for dental curing. The gun unit may be operated by alternating current power or by direct current power supplied by a rechargeable battery power. A relatively short light guide or probe is removably mounted at the front end of the un unit for transmitting the curing light from the gun unit to the location at which photocuring is required. For a system with a stationary light generating device, the light is transmitted from the light generator by an elongated flexible guide to the curing location. A short guide or probe again may be adapted at the free end of the elongated light guide for carrying out the light curing operation at a location remote from the stationary light generator. The short probe or guide is made of a plurality of optical fibres fused in a glass cladding which maintains the optical fibres in a compact composite bundle. The composite bundle is then covered in a protective sheathing material which also prevents the light travelling through the guide from leaking through its peripheral surface. Silicon or glass or metal is commonly used as the sheathing material for such guides. Such guide or probe construction is, for example, shown in U.S. Pat. No. 4,846,546 by Joseph Cuda. The main drawbacks of such common guide or probe are that they are expensive and difficult to fabricate; and furthermore, the sheathing and cladding deteriorate rapidly under repeated autoclaving sterilization operation particularly when the sterilization operation may not be properly carried out in a general dental office. The sterilization is essential to prevent the transmission of disease virus from a contaminated probe to a patient. Also, such glass cladded probe or guide, particularly after subjected to repeated autoclaving sterilization operations, is breakable, so that it presents a hazard to the patient during use as the breakage of the glass components can occur when the probe is located in the patient's mouth cavity.

SUMMARY OF THE INVENTION

The principal object of the present invention is to provide a light curing guide which is simple in construction and is easy to produce.

Another object of the present invention is to provide a light curing guide which is inexpensive to produce such that it is disposable after use.

Another object of the present invention is to provide a light curing guide which is presterilized and packed in a sterilized packaging such that it does not require sterilization before it can be used by the dentist.

Yet another object of the present invention is to provide a light curing guide which can be produced easily with an injection moulding process.

Still another object of the present invention is to provide a light curing guide which is unbreakable and is safe to use within a patient's mouth cavity without any potential health hazard to the patient.

The disposable probe comprises a generally cylindrical rod made of a plastic material having a low light refraction characteristics. The rod has a light receiving end and a curing end. The light receiving end has larger diameter tapering gently to the curing end which has a smaller diameter, and an arcuate bend portion is formed in the curing end.

BRIEF DESCRIPTION OF THE DRAWINGS

FIG. 1 is a side elevation view of the light curing guide according to the present invention.

FIG. 2 is an end elevation view thereof at the light receiving end.

FIG. 3 is an end elevation view thereof at the curing end.

FIG. 4 is a sectional view of thereof along line IV—IV in FIG. 1.

FIG. 5 is a sectional view thereof along line V—V in FIG. 1.

DESCRIPTION OF THE PREFERRED EMBODIMENTS

With reference to the drawings in which like reference numerals designate corresponding parts in the several views, the light curing guide of the present invention is a generally cylindrical rod 10 made of a clear plastic material having a low light refraction characteristics such that it can transmit light in the range of from 300 nanometers (nm) to 800 nanometers (nm). Light in such range is commonly used in photocuring operations and in particular in the range of 400 nanometers (nm) and 500 nanometers (nm) is used in dental curing operations. Inexpensive amorphous homopolymer such as polymethyl methacrylate and polycarbonate are suitable for such purposes. It has been found that light guides rely on total internal reflection to transmit light efficiently. Total internal reflection occurs if a light wave is incident upon a boundary going from a denser medium of refractive index to a rarer medium of refractive index above a certain angle of incidence. The relationship of the critical angle to the refractive index at a boundary is outlined in the following formula:

$$\mathrm{Sin\ (Theta)} = n1/n2$$

in which
Theta is the critical angle.
n1 is the refractive index of the first medium,
for air n1 is equal to 1.
n2 is the refractive index of the second medium.

Polymethyl methacrylate such as acrylic having a light refractive index of 1.49 in air, the critical angle is 42 degrees, and polycarbonate having a light refractive index of about 1.586, the critical angle is 39 degrees. Thus, these material provide satisfactory light transmission for dental curing purposes.

The rod 10 has a generally circular cross sectional shape and having a larger diameter at the light receiving end 11 tapering gently to a smaller diameter curing end 12. The tapering is, for example, about 2 degrees relative to a plane parallel to the longitudinal axis of the rod 10 as best shown in FIG. 1. The curing end portion 13 is bent at an obtuse arcuate angle from the longitudinal axis of the light receiving end portion 14. The bent portion may have a length, for example, governed by a 60 degrees radian angle as shown FIG. 1. The rod 10, typically has a diameter of from 2 millimeters to 15 millimeters and about 76 mn to 127 mm long. The generally flat surfaces provided at the light receiving end 11 and curing end 12 are smooth clear surfaces to facilitate maximum amount of light transmission.

The tapering shape of the rod 10 enhances the concentration of light transmitted therethrough. Generally, when light is incident upon a boundary going from a denser medium of refractive index to a rarer medium of refractive index, the incident light must be within a critical angle to be reflected totally from the boundary. For acrylic material having a refractive index of 1.586, the critical angle is about 39 degrees. The relatively small tapering angle of the surface of the rod 10 ascertains that the critical angles for the guide will not be exceeded over the length of the guide, so as to limit the light losses through the boundary to a minimum.

The obtuse arc in the curing end portion from the light receiving end portion also reduces the light losses through the peripheral surface. The equation that relates the minimum bend radius in a guide for not theoretical light losses through the surface with light beam passing therethrough is as follows:

$$R = D*(n1+n2)/2*(n1-n2)$$

in which
- $D$ = Diameter of the rod.
- $n1$ = Refractive index of the rod material.
- $n2$ = Refractive index of the cladding.
- $R$ = Center radius of the bend.

since no claddings is provided on the rod 10, the refractive index for $n2$ is 1 for air, and a relatively large arc will considerably reduce the surface light losses.

Following the formation of the rod 10 by injection moulding, it is then cleaned to ascertain a clean surface to reduce any light scattering effects from uneven surfaces and the adherence of dust particles thereon. It is then packaged in a sealed envelope and the entire package is subjected to proper and fully controlled sterilization by radiation or autoclaving. Since the guide is completely sterilized, it does not require further sterilization by the dentist before being used. Thus, a clean and properly sterilized guide is provided for ready use without presenting any health hazard to the patient. It does not depend upon the sterilization operation to be carried out by the dentist such as in the known photo-curing guide. Such user sterilization operation often is unsatisfactorily and/or carelessly carried out so that it can present a serious health hazard to the patient. Furthermore, since the guide can be made inexpensively with the above process, it is not intended for re-use, therefore, a highly clean and disposable curing guide is provided.

The guide may be coupled to a curing gun of a portable curing unit or the free end of the elongated flexible light guide of a stationary curing light unit through a mounting adaptor. A suitable filter may be provided in the adaptor for heat filtering or other desirable purposes.

The bending in the guide enhances the location of its curing end onto the curing location within the patient's mouth cavity for on-the-spot dental curing.

Whilst in the illustrated embodiment presently preferred features of the invention have been put forward herein, it is to be understood that the invention is not limited to the precise forms illustrated herein as an example, and that chances may be made thereto without departing from the spirit and substance of the invention.

I claim:

1. A method of making a disposable dental curing guide comprising,
   moulding a rod member with a amorphous homopolymer material having a low refractive characteristics, said rod member having a larger cross sectional dimension at one end than a second end, and having peripheral surfaces tapering towards said second end, an arcuate bend formed in the proximity of said second end, said one end and said second end having a substantially flat end surface,
   cleaning said rod member to eliminate any contamination and foreign particles on all surfaces thereof,
   placing said rod member in a disposable container,
   sealing said container,
   sterilizing said rod member sealed in said container by subjecting said container with said rod member sealed therein to radiation sterilization.

* * * * *